United States Patent [19]

Higo et al.

[11] Patent Number: 4,979,394

[45] Date of Patent: Dec. 25, 1990

[54] NON-DESTRUCTIVE INSPECTION METHOD

[75] Inventors: Yakichi Higo, Tokyo; Shigetomo Nunomura, Yokohama; Toshio Takano; Junichiro Matsuoka, both of Machida; Tadashi Ashida, Yokohama, all of Japan

[73] Assignees: Nissan Motor Co., Ltd.; Tokyo Institute of Technology, Reasearch Laboratory of Precision Machinery and Electronics, both of Yokohama, Japan

[21] Appl. No.: 232,167

[22] Filed: Aug. 15, 1988

[30] Foreign Application Priority Data

Aug. 14, 1987 [JP] Japan .................. 62-202670

[51] Int. Cl.⁵ .................. G01N 9/24
[52] U.S. Cl. .................. 73/602
[58] Field of Search .......... 73/588, 598, 602, 579, 73/604

[56] References Cited

U.S. PATENT DOCUMENTS

| 4,043,176 | 8/1977 | Graham | 73/587 |
| 4,513,622 | 4/1985 | Uretsky | 73/664 |

FOREIGN PATENT DOCUMENTS

| 0068521 | 1/1983 | European Pat. Off. |
| 2022827 | 12/1979 | United Kingdom |

OTHER PUBLICATIONS

Osaka Science and Technical Center, *High Quality Constructional Bonding Material Development and Research Report*, Mar. 1985, pp. 388–399.

*Primary Examiner*—Hezron E. Williams
*Assistant Examiner*—Louis M. Arana
*Attorney, Agent, or Firm*—Foley & Lardner, Schwartz, Jeffery, Schwaab, Mack, Blumenthal & Evans

[57] ABSTRACT

The coherence between inputted and received white noise is used to determined the presence or absence of flaws in a structure such as a joint. The strength of the joint is determined by integrating the coherence factor and observing the magnitude of the same.

7 Claims, 5 Drawing Sheets

NON-DESTRUCTIVE INSPECTION METHOD

BACKGROUND OF THE INVENTION

1. Field of the Invention

The present invention relates to a non-destructive inspection method and more specifically to such a method which determines the coherence factor between inputted and received waves and which enables the both the presence or absence of a fault and the strength of a joint (or the like), to be ascertained without superficial damage and the like to the item under inspection.

2. Description of the Prior Art

Non-destructive inspection methods have included hammering, X-ray, ultrasonic and the like techniques. These techniques however have suffered from the common drawback that even though cracks can be detected, the actual strength of the joint or element under inspection cannot be ascertained.

The hammering detection technique further encounters the drawback that, when used on a production line, important protective films and coatings tend to be damaged and thus cannot be used with any satisfaction particularly on 100% inspections.

X-ray inspection techniques require extensive shielding in order to protect the health of nearby workers. This of course, apart from providing a potential health hazard increases the cost and complexity of the line.

In the case of ultrasonic detection, noise generated by nearby devices tends to interfere with the accuracy of the system and thus requires special shielding and/or measures to be implemented.

SUMMARY OF THE INVENTION

It is an object of the present invention to provide a non-destructive inspection method which does not pose a health hazard, which can be used without the provision of extensive shielding, which does not damage protective/aesthetic films and the like, and which more importantly can determine the strength of a joint or a like structure.

In brief, the above object is achieved by a method wherein the coherence between inputted and received white noise is used to determine the presence or absence of flaws in a structure such as a joint. The strength of the joint is determined by integrating the coherence factor and observing the magnitude of the same.

More specifically, a first aspect of the present invention is deemed to be in a method of inspection which features the steps of: disposing an input transducer against a sample to be tested and inputting elastic waves into the sample; disposing a receiving transducer on the sample and detecting the waves which have been inputted; determining the coherence factor between the inputted and received waves; determining the physical properties of the sample based on the magnitude of the coherence factor.

A second aspect of the invention is deemed to be in the above method further comprising the steps of: integrating the coherence factor; and determining the strength of the sample based on the magnitude of the integrated coherence factor.

A third aspect of the invention is deemed to be in a method of inspection which features the steps of: disposing an input transducer against a sample to be tested and inputting white noise into the sample; disposing a receiving transducer on the sample and detecting the inputted noise; determining the coherence factor between the inputted and received noise; determining the physical properties of the sample based on the magnitude of the coherence factor.

Another aspect of the invention is deemed to be in the method mentioned immediately above further comprises the steps of: integrating the coherence factor; and determining the strength of the sample based on the magnitude of the integrated coherence factor.

A further aspect of the invention is deemed to be in a method of inspection comprising the steps of: disposing a wave input transducer and a wave receiving transducer in tight contact with preselected sites on a sample; inputting elastic waves containing an effective frequency component into the sample by way of the input transducer; receiving the elastic waves transmitted through the sample; determining the coherence factor of the received wave with respect to the inputted wave; determining a physical property of the sample based on the magnitude of the coherence factor.

DETAILED DESCRIPTION OF THE PREFERRED EMBODIMENTS

Figure 1:
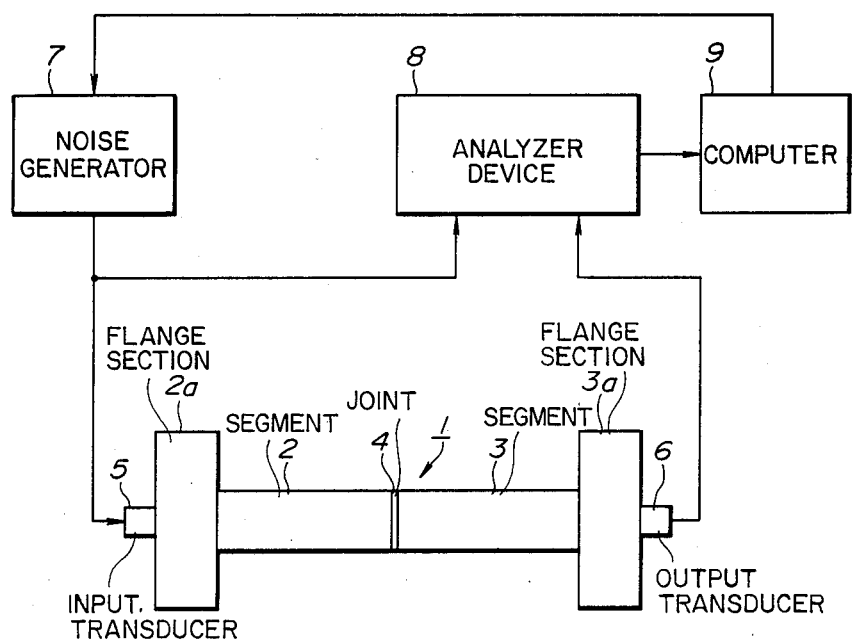
FIG. 1 shows in schematic form the arrangement of a first embodiment of the present invention.
Figure 2:
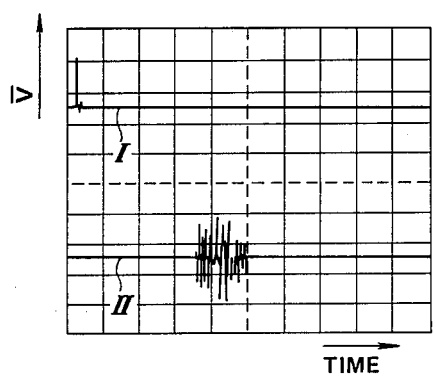
FIG. 2 is a chart showing the input and received waves plotted with respect to time.

FIGS. 1 to 6 show a first test example use to demonstrated the inspection method according to the present invention. In FIG. 1 test samples generally denoted by the numeral 1 comprised first and second segments 2 and 3 which were connected to define a joint section 4. In this instance, the segments 2 and 3 were bonded together using a epoxy type adhesive which contains an alumnia compound.

Two of the above type of test sample were prepared, the first in a manner which ensured a good joint and the second in manner wherein a silicon mould releasing agent was purposely introduced into the joint in a manner to ensure the formation of a major defect.

In both cases the first and second segments 2 and 3 were formed of stainless steel rod having a diameter of 14 mm and a length of 60 mm. Each rod was provided with a flange section at one end. In this instance the flanges 2a, 3a had a diameter of 48 mm and a thickness of 12 mm. The end faces of the two segments, viz., the faces which were joined to form the joint 4 and the end faces of the flange sections were finished using a surface grinder.

Each of the samples was then inspected via technique wherein an input transducer 5 was disposed in closed contact with the end face of the flange section 2a via a thin oil film. An output transducer (pickup) 6 was disposed in a similar manner against the end face of the flange section 3a via a thin oil film. A signal transmitter (e.g. noise generator) 7 was connected to the input transducer 5 and arranged to produce a signal the frequency of which was varied over a range of 0.001 MHz to 2.0 MHz. The output transducer 6 was connected to a Fourier transform analyser 8 (in this instance a MS430 model produced by Anritsu). The output of the noise generator 7 was also connected with the Fourier transform analyzer 8.

The output of the just mentioned analyser device was operatively connected to a 16 bit computer 9 (in this instance a PC9801 model produced by NEC) which was programmed to determine the coherence factor C at predetermined intervals over the above mentioned frequency range. The computer 9 was also connected to the noise generator 7 in order to facilitate control of the signal output.

During each of the tests the noise generator 7 was operated in manner wherein impulse waves containing an effective wave component (see I in FIG. 2 by way of example) were input in the form of elastic waves via the input transducer 5 and subsequently received by the pickup or receiving transducer 6. An example of the received wave form is denoted by II in FIG. 2.

It should be noted that, in order to remove the wave reflected on the internal surfaces of the sample, trimming was effected within a predetermined time region.

Figure 3:
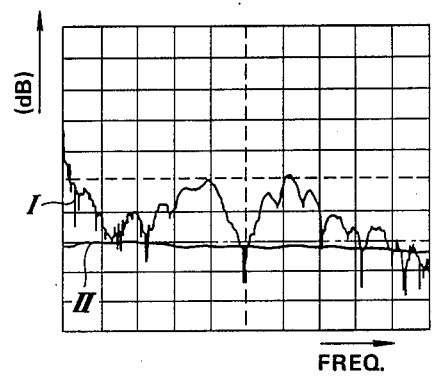
FIG. 3 is a chart showing the changes in the input and received waves with respect to frequency.

FIG. 3 discloses the frequency spectra of the input and received waves I, II.

Figure 4:
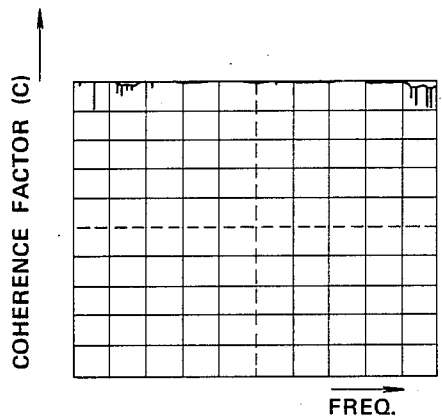
FIGS. 4–6 are charts which show the results obtained when the instant invention was used to inspect a first type of test sample.
Figure 5:
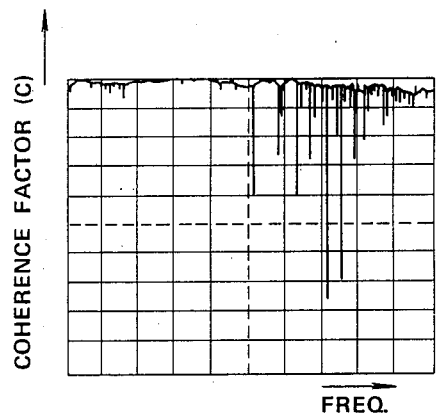

The values of coherence factor C of received wave II with respect to the input signal I for each sample was determined at given intervals over the predetermined frequency range and recorded in the computer 9. Following this, each value was integrated and plotted against fracture stress (see FIG. 6). FIG. 4 shows an example of the coherence factor results provided by the "good" type sample while FIG. 5 shows those obtained with the "defective" type sample which was deliberately rendered faulty.

Following this test, both types of samples were destructively tested by applying tension with an Instoron tensile strength tester until breakage occured. In the case of the "good" sample which provided the results shown in FIG. 4 the braking strain was 3.2 Kg/mm$^2$; while in the case of the "defective" sample which provided the results shown in FIG. 5, the breaking strain was only 0.9 Kg/mm$^2$.

These tests indicated that when the coherence factor C is 1 or above, there is no substantial defect in the joint while in the event the value is between 1 and 0, a fault or major defect exists.

Figure 6:
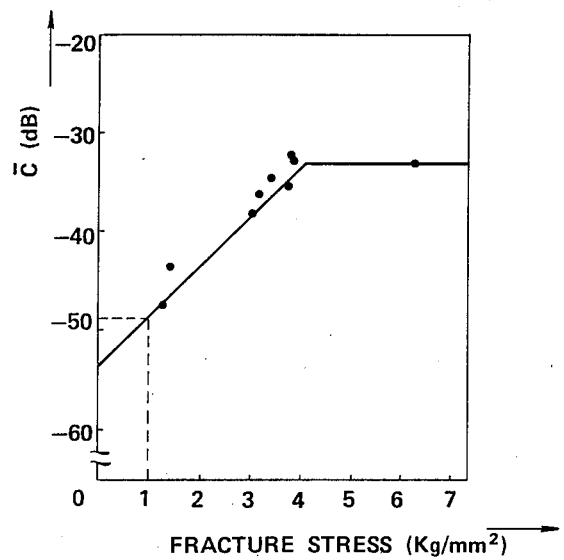

FIG. 6 shows in terms of fracture stress and an integrated coherence factor value C, test results of a plurality of the above type of sample. As will be appreciated from this figure, given that the acceptable minimum strength (viz., peel strength) of the joint is 1 Kg/mm$^2$, samples wherein the integrated value C of the coherence factor C are less than 51 dB, are acceptable.

Figure 7:
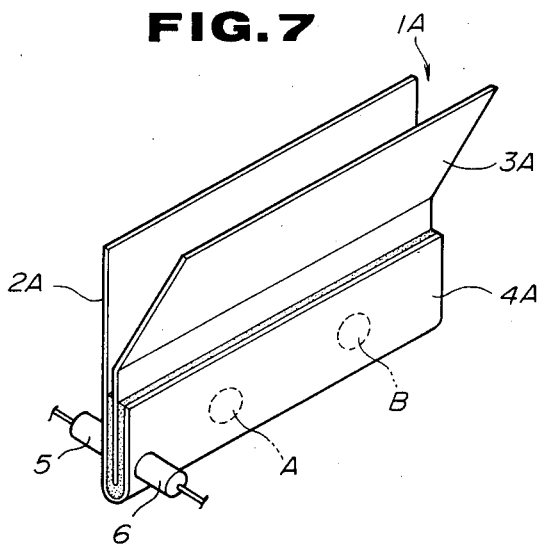
FIG. 7 shows a second test sample used to demonstrate the accuracy and utility of the present invention.
Figure 8:
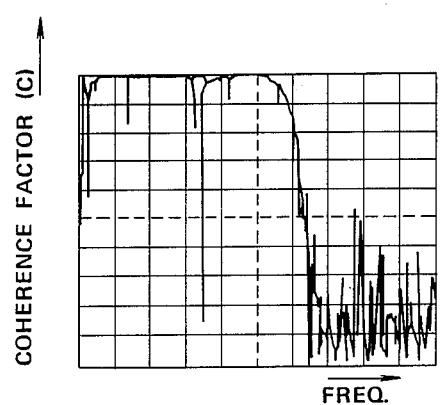
FIGS. 8 and 9 are charts which show the results obtained during inspection of the second embodiment.
Figure 9:
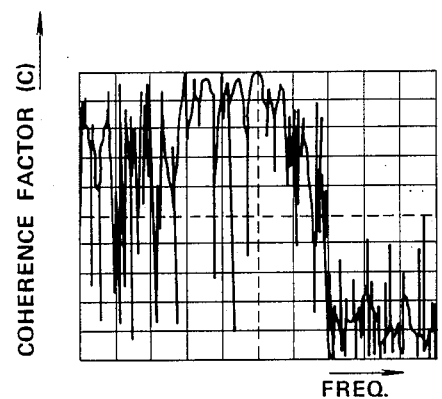

FIGS. 7 to 9 shows a second test example of the present invention. In this instance the test sample was formed by cutting out a section of a lower portion of a vehicle door. As shown in FIG. 7 the sample consisted basically of first and second segments 2A and 3A (outer and inner panels respectively) formed of cold rolled steel sheet having a thickness of 0.8 mm.

A rust preventive sealant 10 (2017T produced by the Nipon Gomu Co) having an adhesive function had been applied to the inner surface of one side edge of the first segment 2A. In addition to this, the side edge of the first segment 2A had been hemmed against the second segment 3A to define a joint 4A. The joint 4A after being formed had been subject to electrodeposition painting and heating at 70° C. for 30 minutes. This process ensured that rust-preventing layers were dryed and hardened.

In order to develop a fault section, section B (shown circled in broken line) was exclusively heated to 300° C. for 30 seconds and then rapidly cooled to −40° C. to artificially induce cracking and thus establish a defective area. Section A, on the other hand, was filled with sealant 10 and non-defective.

The sample was then tested by sequentially sandwiching sections A and B between the input transducer 5 the pickup 6. As in the previous case, a thin oil film was formed on the surfaces of the segment 2A in a manner to establish a good transducer connection. The noise generator 7 was then induced to produce white noise over a spectrum ranging from 0.25 to 2 MHz (by way of example).

Accordingly, elastic waves were passed through the sample from the input transducer 5 to the pickup 6. The coherence factor C was determined at predetermined intervals over the above mentioned range and the values recorded and subsequently integrated. The results of these tests are shown in FIGS. 8 and 9. As will be appreciated from these figures, while the coherence factor C predominantly remains at or above 1 the section of the joint under test is indicated as being non-defective, while in the event that the coherence factor falls below 1 the cracks or the like defects are indicated.

As indicated previously in connection with FIG. 6, while the value of the coherence factor is 1 or above a given joint strength is indicated.

Figure 10:
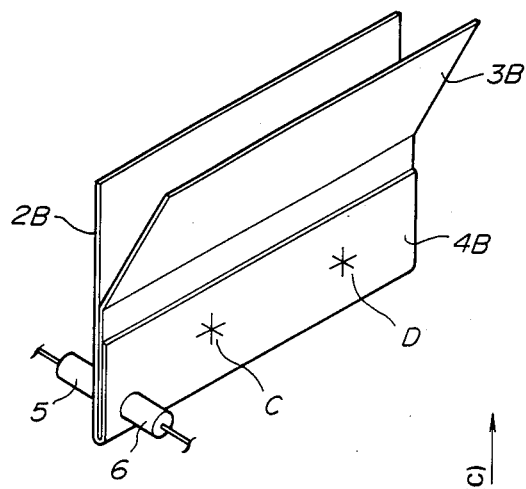
FIG. 10 shows a third test sample used to demonstrate the features of the present invention.
Figure 11:
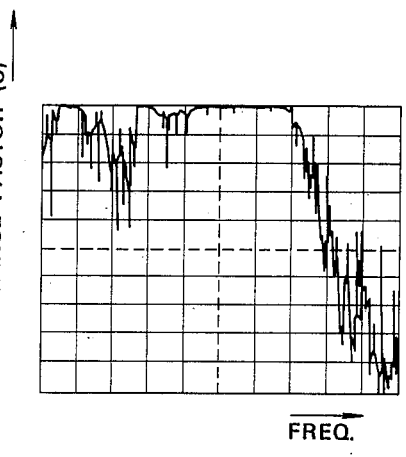
FIGS. 11 and 12 show the results obtained when inspecting the third test sample.
Figure 12:
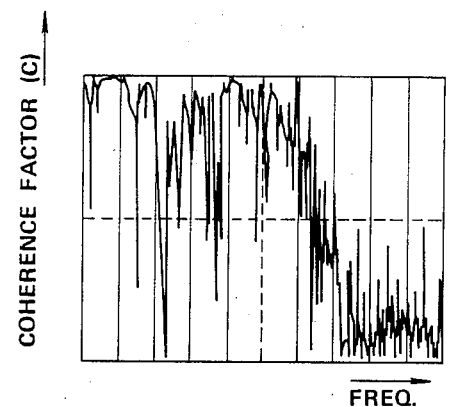

FIGS. 10 to 12 show a third test example used to demonstrate the accuracy and utility of the present invention. This test sample is basically the same as the second one and differs in that instead of heating and cooling to develop a faulty section, the test sites were prepared by spot welding site C in an appropriate manner—viz., spot welding using a current of 10,000 amp. for 10 cycles at a pressure of 200 Kgf.; while site D, on the other hand, was spot welded using a current of 60,000,000 amp. for 10 cycles at a pressure of 200 Kgf.

The input transducer 5 and the pickup 6 were then placed in contact with each of the sites via a thin oil film. Testing of the two sites C and D was then carried out in a manner essentially as described with the preceeding two test samples.

The results of these tests are shown in FIG. 11 and 12. FIG. 11 shows the test results for site C while FIG. 12 shows those obtained with site D.

From these figures it is again clearly evidenced that while the coherence factor remains predominantly at or above 1 appropriate physical properties are indicated while in the event that the value was below 1 defects were indicated.

It will be understood that the invention is not limited to the examples disclosed hereinabove and that the concept thereof can be applied to various types of joints and the like. For example, the present invention can be utilized to test continous welds or the like produced by arc or beam welding, ultrasonic welding, rivetting and the like. Further, a plurality of different elastic waves can be used over different frequency spectrums in order to derive more detailed data. The various other possibilities possible will be clear to those skilled in the and art to which the present invention pertains and as such no further disclosure will be given for brevity.

What is claimed is:

1. A method of inspection comprising the step of:
    disposing an input transducer against a sample to be tested and inputting elastic waves into said sample;
    disposing a receiving transducer on said sample and detecting received waves which have been transmitted through said sample;
    determining a coherence factor which is indicative of the coherence between said elastic waves and said received waves; and
    determining the physical properties of said sample based on the magnitude of said coherence factor.

2. A method as claimed in claim 1 further comprising the steps of:
    varying the frequency of said elastic waves over a preselected frequency range;
    determining said coherence factor at predetermined intervals over said predetermined range.

3. A method as claimed in claim 1 wherein said sample includes a joint and wherein said input transducer and said receiving transducer are arranged so that said elastic waves pass through said joint and further comprising the steps of:
    integrating said coherence factor; and
    determining the peel strength of said joint by comparing the magnitude of said integrated coherence factor with a predetermined value.

4. A method of inspection comprising the step of:
    disposing an input transducer against a sample having a joint to be tested and inputting white noise into said sample;
    disposing a receiving transducer on said sample and detecting the received noise which has passed through said joint from said input transducer;
    determining a coherence factor which is indicative of the coherence between said white noise and said received noise; and
    determining the physical properties of said joint based on the magnitude of said coherence factor.

5. A method as claimed in claim 4 further comprising the steps of:
    integrating said coherence factor; and
    determining the peel strength of said joint by comparing the magnitude of said integrated coherence factor.

6. A method of inspection comprising the steps of:
    disposing a wave input transducer and a wave receiving transducer in tight contact with preselected sites on a sample said preselected sites being selected so that a joint formed in said sample is located between said sites;
    inputting elastic waves containing an effective frequency component into said sample by way of said input transducer;
    receiving elastic waves transmitted through said sample;
    determining a coherence factor which is indicative of the coherence between said received waves with respect to said inputted waves;
    determining physical properties of said sample based on the magnitude of said coherence factor.

7. A method as claimed in claim 6 further comprising the steps of:
    integrating said coherence factor;
    determining the peel strength of said joint based on the magnitude of said integrated coherence factor.

* * * * *